US007613662B2

(12) United States Patent
Tsirigos et al.

(10) Patent No.: US 7,613,662 B2
(45) Date of Patent: Nov. 3, 2009

(54) APPARATUS, MACHINE-READABLE MEDIUM, AND SYSTEM FOR THE DETECTION OF ATYPICAL SEQUENCES VIA GENERALIZED COMPOSITIONAL METHODS

(75) Inventors: Aristotelis Tsirigos, Astoria, NY (US); Isidore Rigoutsos, Astoria, NY (US)

(73) Assignee: International Business Machines Corporation, Armonk, NY (US)

( * ) Notice: Subject to any disclaimer, the term of this patent is extended or adjusted under 35 U.S.C. 154(b) by 286 days.

(21) Appl. No.: 10/855,367

(22) Filed: May 28, 2004

(65) Prior Publication Data
US 2005/0267692 A1    Dec. 1, 2005

(51) Int. Cl.
*G06N 3/12*    (2006.01)
(52) U.S. Cl. .............................. 706/13; 702/19; 703/2; 706/11; 707/6
(58) Field of Classification Search ........................ None
See application file for complete search history.

(56) References Cited

U.S. PATENT DOCUMENTS

2003/0224380 A1* 12/2003 Becker et al. .................. 435/6

OTHER PUBLICATIONS

Samuel Karlin, Allan M. Campbell, and Jan Mrazek, "Comparative DNA Analysis Across Diverse Genomes,"1998, Annu. Rev. Genet., vol. 32, pp. 185-225.
Toshimichi Ikemura, "Codon Usage and tRNA Content in Unicellular and Multicellular Organisms,"1985, Mol. Biol. Evol., vol. 2, No. 1, pp. 13-34.
Mark A. Ragan and Robert L. Charlebois, "Distributional profiles of homologous open reading frames among bacterial phyla: implications for vertical and lateral transmission,"2002, International Journal of Systematic and Evolutionary Microbiology, vol. 52, pp. 777-787.
Samuel Karlin, Jan Mrazek, and Allan M. Campbell, "Codon usages in different gene classes of the *Escherichia coli* genome,"1998, Molecular Microbiology, vol. 29, No. 6, pp. 1341-1355.
Samuel Karlin and Jan Mrazek, "What Drives Codon Choices in Human Genes?,"1996, J. Mol. Biol., vol. 262, pp. 459-472.
Samuel Karlin and Chris Burge, "Dinucleotide relative abundance extremes: a genomic signature,"Jul. 1995, TIG, vol. 11, No. 7, pp. 283-290.
Jeffrey G. Lawrence and Howard Ochman, "Molecular archaeology of the *Escherichia coli* genome," Aug. 1998, Proc. Natl. Acad. Sci. USA,vol. 95, pp. 9413-9417.
Jeffrey G. Lawrence and Howard Ochman, "Amelioration of Bacterial Genomes: Rates of Change and Exchange," 1997, J. Mol. Evol., vol. 44, pp. 383-397.
Sean D. Hooper and Otto G. Berg, "Detection of Genes with Atypical Nucleotide Sequence in Microbial Genomes," 2002, J. Mol. Evol., vol. 54, pp. 365-375.

(Continued)

*Primary Examiner*—Carolyn L. Smith
(74) *Attorney, Agent, or Firm*—McGinn IP Law Group PLLC

(57) ABSTRACT

A method and system for determining whether a sequence fragment g is atypical with respect to a reference sequence G using compositional methods and including constructing a template from G and g respectively containing a sequence of characters for a comparison with one another, wherein a number of characters contained in the template exceeds two. For the case where the sequences at hand are genetic, the atypicality detection can be used to determine whether a given sequence fragment g is the result of a horizontal transfer event.

16 Claims, 12 Drawing Sheets

OTHER PUBLICATIONS

William S. Hayes and Mark Borodovsky, "How to Interpret an Anonymous Bacterial Genome: Machine Learning Approach to Gene Identification," 1998, Genome Research, vol. 8, pp. 1154-1171.

Siv G. E. Andersson and C. G. Kurland, "Codon Preferences in Free-Living Microorganisms," Jun. 1990, Microbiological Reviews, vol. 54, No. 2, pp. 198-210.

Allan Campbell, Jan Mrazek, and Samuel Karlin, "Genome signature comparisons among prokaryote, plasmid, and mitochondrial DNA," Aug. 1999, Proc. Natl. Acad. Sci. USA, vol. 96, pp. 9184-9189.

Santiago Garcia-Vallve, Anton Romeu, and Jaume Palau, "Horizontal Gene Transfer in Bacterial and Archaeal Complete Genomes," 2000, Genome Research, vol. 10, pp. 1719-1725.

S. Garcia-Vallve, E. Guzman, M. A. Montero, and A. Romeu, "HGT-DB: a database of putative horizontally transferred genes in prokaryotic complete genomes," 2003, Nucleic Acids Research, vol. 31, No. 1, pp. 187-189.

Paul M. Sharp and Wen-Hsiung Li, "The codon adaptation index—a measure of directional synonymous codon usage bias, and its potential applications," 1987, Nucleic Acids Research, vol. 15, No. 3, pp. 1281-1295.

Samuel Karlin, Jan Mrazek, and Allan M. Campbell, "Compositional Biases of Bacterial Genomes and Evolutionary Implications," Jun. 1997, Journal of Bacteriology, vol. 179, No. 12, pp. 3899-3913.

* cited by examiner

APPARATUS, MACHINE-READABLE MEDIUM, AND SYSTEM FOR THE DETECTION OF ATYPICAL SEQUENCES VIA GENERALIZED COMPOSITIONAL METHODS

BACKGROUND OF THE INVENTION

1. Field of the Invention

The present invention generally relates to a method of detecting atypical sequence fragments contained in longer one-dimensional sequences composed of letters from a fixed alphabet. More specifically, a method of representing sequences and sequence fragments, as based on an experimentally-determined optimal range of pattern template lengths, in combination with a correlation function and a threshold calculation, improves upon conventional methods for carrying out this task. For clarity purposes, we develop and discuss our method in the case where the said sequences are genomic sequences and in particular DNA: in this case, atypical sequences are generally thought to be the result of horizontal transfer events. But the described method is applicable in a more general context, as this would be immediately apparent to someone skilled in the art.

2. Description of the Related Art

As already mentioned above, the system and method that we describe below is generally applicable to the case where a long sequence comprised of letters from a given alphabet contains a fragment which is "atypical," i.e. unlike the remainder of the sequence. For the purpose of presenting a clear description of the approach, we have selected to develop the discussion for the specific case where the sequences at hand are genetic sequences, and in particular DNA; therein we seek to locate atypical sequence fragments. Generally, atypical sequence fragments overlap with regions defining genes but this is not a requirement.

Let us now continue our discussion in the context of genomic sequences and complete genomes. In recent years, an increasing number of the genomes for a number of organisms has been experimentally determined. Through study of these genomic sequences and with the help of other types of analyses, it has been discovered that organisms can acquire genetic sequences from organisms that are not necessarily related to them, through a process that has been termed "horizontal gene transfer" (HGT) or "lateral gene transfer" (LGT). In the discussion that follows, the terms "horizontal gene transfer" and "lateral gene transfer" and the abbreviations HGT and LGT will be used interchangeably.

An exemplary problem addressed by the present invention is that of determining whether an observed genetic sequence from an organism is native to that organism's genome or represents an "atypicality" acquired through the HGT process. And as already mentioned, this exemplary problem is a special case of the problem of identifying atypical sequence fragments within longer sequences.

Before proceeding with a discussion of the present invention, it is noted that a genome can be thought of as a sequence of nucleic acids; among other things, a genomic sequence contains the definitions of the corresponding organism's genes. The above-mentioned exemplary problem, therefore, can be described as the process of deciding for a given segment of a given genetic sequence, referred to as the "query," whether the sequence has been native to the organism's genome or is the result of a transfer event. The query could be distinct from a gene coding region, partially overlapping a gene coding region, or wholly-contained within a gene coding region.

This scenario is analogous to the problem of determining which words, if any, from a given sequence of natural language words have actually originated in another language. It is noted that this 'donor' language may not be known necessarily. The sought determination is to be made by looking at the words, and, without knowing the meaning of each word nor having a dictionary upon which to rely in order to make the decision. Analogously, in the specific problem under consideration that we use to develop our method, and since genomic sequences are available for only a relatively small number of organisms, one cannot rely on the availability of a repository of reference sequences. In general, it is entirely possible that a given genetic sequence has been transferred horizontally from a donor organism whose genome has yet been sequenced.

Techniques for determining whether a genetic sequence of a given size is atypical have been known and will be discussed shortly. However, there is a growing need for new methods that exhibit an increased sensitivity in detecting genetic atypicalities while at the same time reducing the number of false positive predictions.

The present invention addresses the problem of characterizing a sequence fragment of a given sequence in terms of its atypicality. We develop the invention for the concrete case where the given sequence is a genome sequence. Recall that for a given organism, those genomic fragments whose origin can be traced to an exogenous source, with high probability, are ideal candidates for being atypical and putative instances of horizontal gene transfer (HGT).

SUMMARY OF THE INVENTION

In view of the foregoing, and other, exemplary problems, drawbacks, and disadvantages of the conventional systems, it is an exemplary feature of the present invention to provide a system and method in which detection of atypical sequences is improved over conventional methods.

It is another exemplary feature to provide a template having optimal length for purpose of detecting atypical sequences.

To achieve the above and other features, in a first exemplary aspect of the present invention, described herein is a method and system for detecting atypical sequence fragments, the method including constructing a template that subselects a sequence of characters from a sequence under evaluation, wherein a number of characters contained in the template exceeds two.

In a second exemplary aspect of the present invention, also described herein is a method for representing a genetic sequence, including constructing a template containing a sequence of genetic characters for a comparison, counting the number of occurrences of the template in the genetic sequence, and recording a representation of the genetic sequence being evaluated as a feature vector comprising a sequence of number of occurrences of at least one template, wherein a minimum number of the characters contained in the template is two.

In a third exemplary aspect of the present invention, also described herein is a signal-bearing medium tangibly embodying a program of machine-readable instructions executable by a digital processing apparatus to perform a method of detecting horizontal gene transfer in an organism, the program including a feature vector calculator module to compute the number of occurrences of at least one template in a sequence under evaluation and a memory interface module to retrieve the genetic sequence under evaluation from a memory and to record the number of occurrences of the template in the genetic sequence under evaluation, wherein the template contains at least two characters.

With the above and other unique and unobvious exemplary aspects of the present invention, it is possible to improve the detection of atypical sequence fragments. For the special case where the query sequence coincides with the extent of a gene coding region, the present invention permits the elucidation of putative HGTs.

BRIEF DESCRIPTION OF THE DRAWINGS

The foregoing and other purposes, aspects and advantages will be better understood from the following detailed description of an exemplary embodiment for the special instance where the invention is applied to the problem of identifying LGT's, with reference to the drawings, in which.

DETAILED DESCRIPTION OF AN EXEMPLARY EMBODIMENT OF THE INVENTION

Figure 1:
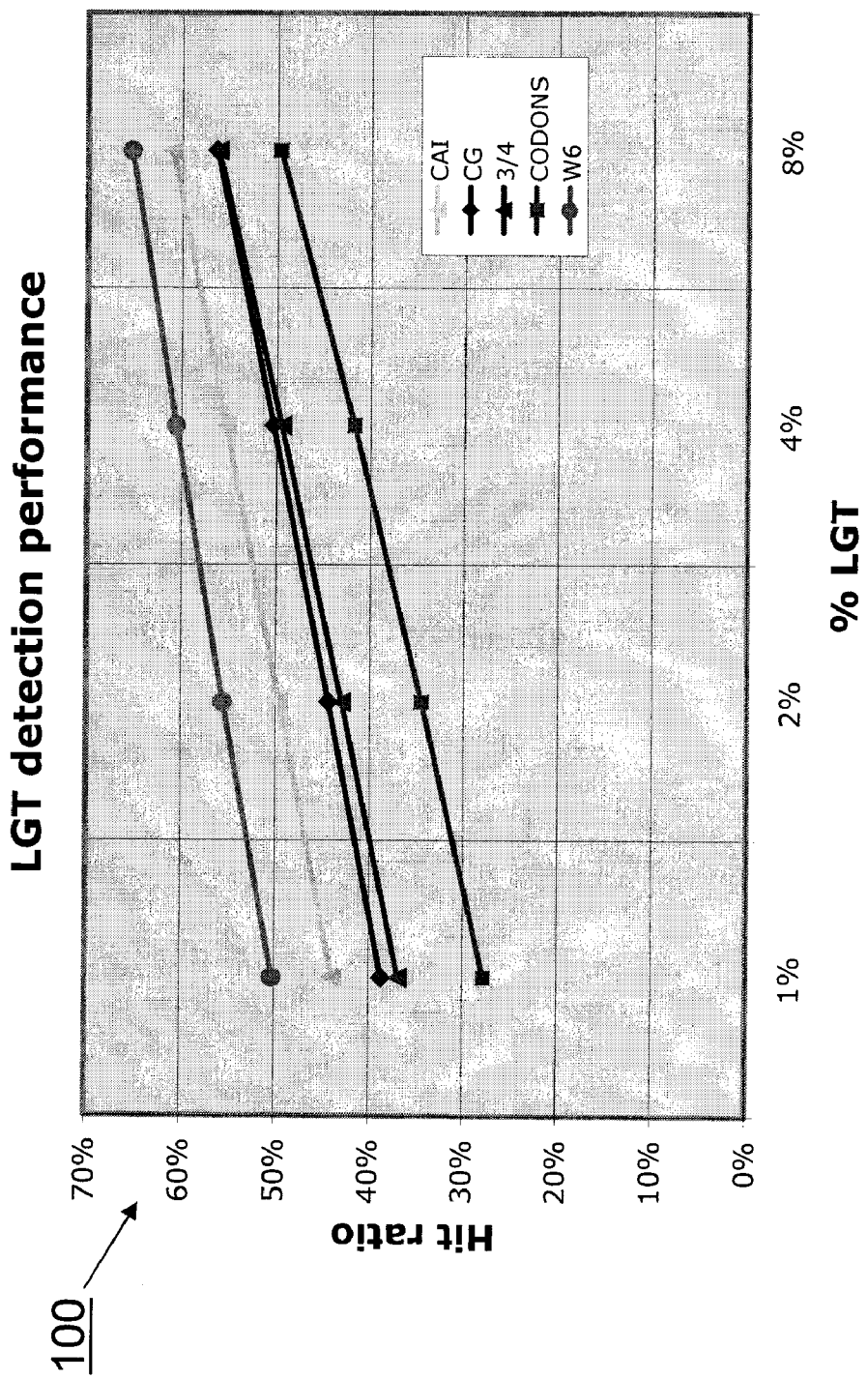
FIG. 1 shows an overall performance result 100 of scoring methods for LGT detection wherein a specific instance of the present invention is compared with four conventional methods.

Referring now to the drawings, and more particularly to FIGS. 1-12, exemplary embodiments of the present invention will now be described.

The present invention evolved from an effort by the present inventors to study and improve conventional methods for detecting atypicalities. For the special case where the atypicalities corresponded to putative LGTs, as described below, the present inventors have carried out considerable experimentation to determine an optimal range for template lengths appropriate for this task.

In the following discussion, an alternative representation scheme is presented that is based on a sequence's composition. A focus is on devising novel methodologies which can help identify sequences with atypical features (e.g., genes whose features deviate from those of the majority of the genes in the genome under consideration). In the case of genomic sequences, the underlying conjecture is that such atypical genes are most likely the result of lateral transfer events. An extensive set of experiments with 123 archaeal and bacterial genomes is described and demonstrates that in the special instance of studying the problem of horizontal transfers, the present method exhibits a markedly improved ability in identifying horizontally-transferred genes, when compared to previous reported approaches.

In addition, it is shown that improvement generally increases with the size of the templates that are used as features and in conjunction with an appropriate similarity metric. For the case of genetic sequences, it appears that an optimum set of conditions exists, as we discuss below, and that further increase in template size leads to a decrease in performance. Finally, the method is demonstrated as being extended to cover the case where, instead of individual sequence fragments, the objective is to detect clusters of atypical sequence fragments (e.g. groups of genes that appear close to one another in the genome of the receiving organism).

In recent years, the increase in the amounts of available genomic data has made it easier to appreciate the extent by which prokaryotes make use of horizontal gene transfer in order to increase their genetic diversity. Horizontally transferred genes give rise to extremely dynamic genomes in which substantial amounts of coding DNA are incorporated into the chromosome from external sources. Unlike eukaryotes, which evolve principally through the modification of existing genetic information, prokaryotes seem to have obtained a significant proportion of their genetic diversity through the acquisition of sequences from organisms to which they can be rather distantly related. Thus, in principle, horizontal gene transfer has the potential to produce extremely dynamic genomes in which substantial amounts of DNA, exogenous in origin, are inserted in the chromosome. Such transfers have the potential to change both the ecological and the pathogenic character of archaea and bacteria.

The significance of horizontal gene transfer for prokaryotic evolution was not recognized until the 1950s, when pathogenic bacteria began developing multi-drug resistance patterns, on a worldwide scale. The ease with which certain bacteria developed resistance to the same spectrum of antibiotics indicated that these traits were being transferred across taxa, rather than being generated de novo by each lineage.

It was not until much later that the widespread impact of horizontal gene transfer on prokaryotic evolution was adequately appreciated. These early attempts to study rapid evolution by gene acquisition encompassed four issues that have since become central to all subsequent analyses.

First, it is imperative to devise methods for detecting and identifying cases of horizontal gene transfer. Second, one would ideally like to determine the source organism for each one of the horizontally-transferred genes. Third, it is essential to understand how many and which traits have been conveyed to the host genome as a result of the identified transfer events. Fourth, one would like to estimate the relative rates at which different classes of genes mobilized across genomes.

Naturally, to establish whether a new trait, or a specific region in a genome is the result of horizontal transfer processes, it would be most satisfying if one could observe the conversion of a deficient strain in the presence of an appropriate donor. It would be all the more convincing to establish that genetic material had indeed been transferred and also to determine the manner in which it was acquired.

But, in the absence of controlled experimental settings, actual transfer events cannot be easily pinpointed. Thus, unambiguous evidence of their occurrence must be derived from other sources. And this have given rise to a number of techniques that have been developed for the detection of genetic exchange events across species, and which go after their goal by processing sequence data.

Horizontally-transferred genes share an unusually high degree of affinity with the donor organism. Moreover, both donor and recipient genomes are expected to share every trait that is associated with the genes in question. Since each transfer event involves the introduction of DNA into a single lineage, the acquired trait(s) will be limited to the descendents of the recipient strain and will remain absent from closely related taxa. This will, in turn, produce a scattered phylogenetic distribution.

On the other hand, horizontal gene transfer need not be invoked as the causal agent in attempts to explain the sporadic occurrence of certain phenotypic characteristics, (e.g., the ability to withstand particular antibiotics). In fact, these properties can frequently originate through point mutations in existing genes and, therefore, may be the result of independent evolution in diverging lineages.

Frequently, additional information has been brought to bear in an effort to distinguish between convergent evolution and horizontal gene transfers. It should come as no surprise that the strongest evidence for (or against) horizontal gene transfer derives from a genetic analysis of the implicated DNA sequences.

DNA sequence information has been used in diverse ways to identify cases of horizontal gene transfer, but the approach underlying most proposed analyses is the discovery of features indicating that the evolutionary history of genes within a particular region differs substantially from that of ancestral (i.e., vertically-transmitted) genes.

Similarly to distinctive phenotypic properties, DNA segments gained through horizontal gene transfer often display a restricted phylogenetic distribution across related strains or species. In addition, these species-specific regions may show unduly high levels of DNA or protein-sequence similarity to genes from taxa that are inferred to be very divergent by means of other criteria. The significance of aberrant phylogenies can be evaluated by phylogenetic congruency tests or other means.

Although gene comparisons and their phylogenetic distributions can be useful in detecting horizontal transfers, it is the DNA sequences of the genes themselves which provide the best clues as to their origin and ancestry. Prokaryotic species display a wide degree of variation in their overall G+C content, but the genes in a particular species' genome are fairly similar with respect to their base composition.

Similar observations have been made for patterns of codon usage and the frequencies of di- and trinucleotides. Consequently, any sequences that may have been introduced in a genome through recent horizontal transfer ought to retain, at least initially, the sequence characteristics of the donor genome and thus could, in principle, be distinguished from the DNA that has been ancestrally present in the recipient genome through examination of the actual nucleotide sequence.

It is not surprising that genomic regions often manifest several attributes which are tell-tale signs of their acquisition through horizontal gene transfer. For example, there is a large number of S. enterica genes that are absent from E. coli (as well as other enteric bacteria) and which have base compositions that are significantly different from the average G+C content (=52%) of S. enterica's genome. Also, certain serovars of S. enterica may contain more than a million bases not present in other serovars, as assessed by a genomic subtraction procedure.

The base compositions of these anonymous, serovar-specific sequences suggest that at least half of them are the result of horizontal transfer events. Additionally, the regions adjacent to these putative horizontal transfers often contain vestiges of sequences facilitating their integration in the recipient's genome, such as remnants of transposable elements, transfer origins of plasmids, or known attachment sites of phage integrases. All this orthogonal evidence further attests to the sequences' foreign origin.

In what follows, a novel methodology is presented that is based on genomic composition and can identify atypical sequence fragments. We showcase the methodology in the special case of identifying putative horizontally-transferred genes. With the help of a very extensive set of experiments with 123 archaeal and bacterial genomes we also demonstrate that this method, heretofore referred to as Wn, outperforms previously published approaches, such as C+G and its variations, dinucleotides, and CAI.

Before outlining the details of the present invention, we begin with a brief overview of previously reported methods for identifying atypical genetic sequences and which methods have been based on genomic composition. We then follow the description of the Wn technique of the present invention with a description of experiments and the reporting of obtained results on a collection of 123 genomes; these results make very apparent the improvement over traditionally used methods that can be achieved by the Wn technique.

An Overview of Composition-Based Methods

Previously published methods for horizontal gene transfer detection which have been based on gene content assume that in a given organism there exist compositional features that remain relatively unchanged across its genomic sequence. Genes that display atypical nucleotide composition compared to the prevalent compositional features of their containing genome are likely to have been horizontally acquired.

Consequently, over the years, multiple features have been used to define characteristic 'signatures' for a genome: once such a signature has been computed, any sequence fragment that deviates from it can be marked as a horizontal transfer candidate.

The simplest and historically earliest type of genomic signature is its composition in the bases G and C (i.e. the genome's G+C content). It is important to note that due to the periodicity of the DNA code, implied by the organization of the coding regions into codons, the G+C content varies significantly based on the position within the codon. As a result, four discrete G+C content signatures can be identified. The first of the four G+C signatures corresponds to the overall G+C content and is computed by considering the entire nucleotide sequence of a genome, and includes both coding and non-coding regions. The remaining three signatures are denoted by G+C(k), k=1,2,3 and correspond to the value of the G+C content as determined by considering only those nucleotides occupying the k-th position within a codon. Unlike the first of these four signatures, only coding regions are used in the computation of G+C(k).

A related variation of the G+C(k) content idea is the so-called Codon Adaptation Index (CAI) which was introduced by Ikemura in 1985. CAI measures how well a given gene's codon usage correlates with the codon usage of highly expressed genes from the organism under consideration.

In yet another variation introduced in the context of a study of the *E. coli* genome, Lawrence and Ochman identified atypical coding regions by simultaneously combining G+C (1) and G+C(3). Additionally, for each gene they computed a 'codon usage' that assessed the degree of bias in the use of synonymous codons compared to what was expected from each of the three G+C(k) values. A gene was rendered atypical when its relative "codon usage", as defined above, differed significantly from its CAI index.

The codon usage patterns in *E. coli* were also investigated by Karlin et al, who found that the codon biases observed in ribosomal proteins deviate the most from the biases of the average *E. coli* gene. Using this observation, they defined "alien" genes as those genes whose codon bias: a) exceeded a threshold when compared to that of the average gene, and, b) was high relative to the one observed in ribosomal proteins.

Another popular genomic signature is the relative abundance of dinucleotides compared to single nucleotide composition. As demonstrated by Karlin and co-workers, despite the fact that genomic sequences display various kinds of internal heterogeneity, including G+C content variation, coding versus non-coding, mobile insertion sequences, etc., they nonetheless preserve an approximately unchanged distribution of dinucleotide relative abundance values, when calculated over non-overlapping 50-kb-wide windows covering the genome. Moreover, the dinucleotide relative abundance values of different sequence samples of DNA from the same organism are generally much more similar to each other than they are to sequence samples from other organisms. Finally, closely related organisms generally have more similar dinucleotide relative abundance values than do distantly related organisms.

Karlin and co-workers also introduced the "codon signature" which is defined as the dinucleotide relative abundances at the distinct codon positions 1-2, 2-3 and 3-4 (4=1 of the next codon). For large collections of genes (50 or more), they found that the codon signature, like the genome signature, is essentially invariant. The codon signature largely adheres to the genome signature but accommodates amino acid constraints.

Hooper and Berg proposed as a genomic signature the dinucleotide composed of the nucleotide in the third codon position and the first position nucleotide of the following codon. Using the 16 possible dinucleotide combinations, they calculate how well individual genes conform to the computed mean dinucleotide frequencies of the genome they belong to. Mahalanobis distance, instead of Euclidean distance, is used to generate a distance metric on the dinucleotide distribution. As it turned out, genes from different genomes could be separated with a high degree of accuracy.

Hayes and Borodovsky have also demonstrated the connection between gene prediction and atypical sequence detection. While addressing the problem of accurate statistical modeling of DNA sequences as coding or noncoding for bacterial species, they observed that more than one statistical model was necessary to describe the gene-containing regions. This was attributed to the diversity of oligo-nucleotide compositions among the gene coding regions, and specifically the variety of the underlying codon usage strategies. In the simplest case, two models sufficed, one for typical and one for atypical genes. The atypical model that they introduced allowed the prediction of genes which escape identification by the typical model while at the same time suggesting good horizontal transfer candidates.

S. Garcia-Vailve, A. Romeu, and J. Palau, in their 2000 article "Horizontal Gene Transfer in Bacterial and Archaeal Complete Genomes", identified horizontal gene transfer candidates by combining multiple sources of information. In particular, their analysis was based on G+C and G+C(k) content, on codon usage, on amino-acid usage and on gene position. Genes whose G+C content significantly deviated from the mean G+C content of the organism were considered to be candidate gene transfers provided that: a) they also have an extraneous codon usage (computed in a similar way), b) their size is more than 300 bp, and c) the amino-acid composition of the corresponding protein deviated from the average amino-acid composition of the genome. The same authors stress the importance of excluding highly expressed genes from the candidate set of gene transfers, since they may deviate from the mean values of codon usage simply because they must adapt in order to reflect changes in tRNA abundance: for example, ribosomal proteins are filtered and are not included in the predictions.

In a 2003 article, entitled "HGT-DB: a database of putative horizontally transferred genes in prokaryotic complete genomes," S. Garcia-Vallve, E. Guzman, M. A. Montero, and A. Romeu used this method to generate results for 88 complete bacterial and archaeal genomes: the putative horizontally transferred genes were collected in the HGT-DB database that is accessible on the world-wide web.

It should be stressed however, that Garcia-Vallve and co-workers did not introduce a new genomic representation scheme, but rather combined several distinct, previously-published modalities into one feature vector. The complication with this approach, as is always the case with feature vectors comprising distinct non-uniform features, is that it is difficult to derive a distance function which properly takes into account the distinct features, the different units, the different dynamic ranges of values, etc.

In direct contrast to this, the method of the present invention preferably uses a single feature to determine whether a sequence fragment is atypical when compared with the rest of the sequence that contains it.

Before concluding our brief summary of earlier work, we should also mention an approach that is radically distinct from the ones described above in that it is not composition-based. In "Distributional profiles of homologous open reading frames among bacterial phyla: implications for vertical and horizontal transmission", M. Ragan and R. Charlebois organize ORFs from different genome in groups of high sequence similarity (using gapped-BLAST) and look at the distributional profile of each group across the genomes. ORFs whose distribution profile cannot be reconciled parsimoniously with a tree-like descent and loss are candidates for having been transmitted through horizontal gene transfer. In other words, instead of deciding whether a sequence fragment is typical or atypical by comparing its composition to that of the containing genome, they carry out a statistical comparison of similar genes across genomes.

The Wn Method of the Present Invention

We now detail the Wn method of the present invention for deriving generalized compositional features (single modality). The Wn method extends and generalizes composition-based methods in three distinct ways:

first, higher-order tuples of letters are used; this overcomes the diminished discrimination power exhibited by the previously proposed lower-order tuples (e.g. the di- and tri-nucleotide models). Use of richer compositional features leads to an improved ability to classify. It also leads to an increased sensitivity in identifying genes with atypical compositions.

second, in our method, we extend the composition-based model in a manner that allows certain positions of the sequence at hand to be "ignored". This is achieved through the use of generating templates that include "gaps" where each gap is denoted by the "." (also known as the "don't care" character) sequence letters that occupy the "don't care" position are ignored during the computation. As an example, the template A.G which matches each of AAG, ACG, AGG, and ATG will effectively ignore the identity of the nucleotide occupying the middle position.

third, our generalized model permits the consideration and use of templates that do not occupy consecutive positions. For example, in the case of genetic sequences we can use this property to optionally take the periodicity of the DNA code into account: when calculating codon frequencies (through the use of tri-nucleotide templates) one can incorporate the requirement that only the templates that start at positions 3 k+1, where k is a non-negative integer, be examined and participate in any subsequent computations.

In this augmented model, we define the compositional feature vector $\phi(s)$ for any given sequence s over a set of templates $\pi = \{\pi_1, \pi_2, \ldots, \pi_q\}$ as $\phi(s) = (\alpha_1, \alpha_2, \ldots, \alpha_q)$, where $\alpha_i$ is the frequency of template $\pi_i$ in sequence s. Instead of using the absolute template frequencies, these frequencies can be optionally normalized over the expected template frequencies given the expected single nucleotide composition with respect to some background reference sequence. Generally, if g denotes the sequence fragment whose typicality property matches that of G which is the reference sequence, then the single-letter frequencies of the reference sequence G are considered to also match the expected single-letter frequencies of the sequence fragment g. In the case of genomic sequences, g could be a gene or an arbitrary DNA fragment, whereas G could be a genome or part of a genome. The relative (normalized) frequencies are given by the following equation:

$$\alpha_i = \frac{P_g(\pi_i)}{\prod_{j=1}^{|\pi_i|} P_G(\pi_{ij})}$$

where $\pi_{ij}$ is the j-th letter of template $\pi_i$. The probability of the "." character is one. The probability in the numerator is the observed template frequency in the sequence fragment, whereas the single-letter probabilities in the denominator are computed from the reference sequence G; as we have mentioned already, the computations can be carried out with the help of templates that can be made position-specific.

Turning Compositional Features to Typicality Scores

Given a reference sequence G, and a sequence fragment g, the objective is to determine g's "atypicality" with respect to the reference sequence G. It should be noted that, in general, G does not have to be a single sequence of letters, but can be thought of as a collection of $n_G$ fragments—in this case, any computations involving G will be carried out with each of the $n_G$ fragments in turn and the results will be aggregated.

In the case of genomic sequences, we wish to characterize any arbitrary sequence fragment g (whether it corresponds to a coding region, to a non-coding region, or both) in terms of its similarity to G (which can in turn be a whole genome, or part of a genome, or a collection of $n_G$ genomic fragments). The assumption here is that G exhibits a relatively unchanged composition over extended intervals that may not be contiguous necessarily: thus, a sequence fragment g whose template composition differs substantially from the typical composition of the reference sequence G will be considered "atypical" with respect to G.

In our method, a score $S_G(g)$ is assigned to each sequence fragment g as a result of a comparison with G. The higher the score, the more typical g is with respect to G. In the case of genomic data, a sequence fragment with low $S_G(g)$ value is likely to have been acquired through a horizontal gene transfer event from an (generally unknown) donor into G.

Given a sequence fragment's feature vector $\phi(g)$, a straightforward way to compute a typicality score is to compare it with the feature vector $\phi(G)$ of the reference sequence G. The comparison can be performed in multiple ways, and it will yield a score $S_G(g)$ of similarity between g and G.

Four commonly used similarity metrics are correlation, $\chi^2$ test, Mahalanobis distance and relative entropy. The first method involves the calculation of the classic Pearson correlation between the vectors for g and G. In this case, g's score $S_G(g)$ with respect to the reference sequence G can be computed as follows:

$$S_G(g) = \frac{E[(\phi(g) - \mu_{\phi(g)}) \cdot (\phi(G) - \mu_{\phi(G)})]}{\sigma_{\phi(g)} \sigma_{\phi(G)}}$$

The standard $\chi^2$ test measures the deviation of a vector from its expected value by summing up the deviations of each vector component. In this case, g's score is obtained by negating it, so that high $\chi^2$ values (and thus high deviations) will correspond to atypical scores:

$$S_G(g) = -\sum_k \frac{(\phi_k(g) - E[\phi_k(g)])^2}{E[\phi_k(g)]}$$

where the expected value for component k is estimated by the mean value of the component across all $n_G$ segments comprising G (clearly, if G consists of one sequence only, then $n_G = 1$):

$$E[\phi_k(g)] = \frac{1}{n_G} \sum_{g \in G} \phi_k(g)$$

The need to use the Mahalanobis distance arises in the case where the selected compositional features are significantly correlated with each other. As a result their covariance matrix K contains important information. The score induced by the Mahalanobis distance is:

$$S_G(g) = -(\phi(g) - \phi(G))^T K^{-1} (\phi(g) - \phi(G))$$

When the feature vector defines a distribution (e.g. frequencies of all possible tri-nucleotides), a score can be assigned to a fragment g by measuring the distance of the distribution defined by g's vector from the one defined by G's vector using the concept of relative entropy (also known as Kullback-Leibler distance):

$$S_G(g) = -\sum_k \phi_k(g)\ln\frac{\phi_k(g)}{\phi_k(G)}$$

The Wn Method for Atypicality Detection

Given a reference sequence G that comprises $n_G$ segments, one instance of the problem solved by the present invention is to determine the subset of those $n_G$ segments that are deemed atypical. Clearly, the method can be trivially extended to determine whether a given sequence fragment g (not necessarily in G) is atypical with respect to G.

In the case of genomic sequences, the method of the present invention can be used to determine whether a given region g of genome G is the result of a horizontal transfer or not. In another obvious extension, the sequence fragments g correspond to coding regions, i.e. genes. An exemplary goal is to first compute for each gene g in genome G a typicality score with respect to G. This score reflects the similarity of g to the whole genome G as this similarity can be assessed by the selected compositional features.

For our analysis, and in addition to the previously proposed methods (e.g. G+C content, CAI, etc.), we also evaluated the performance of methods which make use of templates of size greater than or equal to 3 (=size of a codon) to form compositional features.

As a first observation, we have found that at template sizes greater than 2, the optimal performance was obtained by not taking the periodicity of the genetic code into account, i.e. by counting all the templates without skipping the $2^{nd}$ and $3^{rd}$ codon positions, and by choosing correlation as the similarity metric for computing the final scores. For template size n, the corresponding method is denoted as Wn, where n is greater that 2.

Furthermore, for genomic sequence data, the performance increased with the template size, reaching a maximum value at sizes 6 through 8 and then dropped sharply as the size increased further. The user has a choice regarding which of the three template sizes (i.e. 6, 7 or 8) to use, and the answer depends on the size of the genomic sequence at hand: short sequences will dictate a value of 6 whereas long sequences will dictate a value of 8.

Clearly, and in order to achieve greater specificity, the largest possible template size should always be opted for, provided that the sequence being processed can yield a substantial number of templates of that size. As a rule of thumb, a lower size template should be used when individual gene transfers are sought, whereas larger size templates should be reserved for when the user tries to identify clusters of laterally transferred genes: a sliding window method to that end is described next.

The Wn variant for atypicallity detection that uses sliding windows Here, for completeness, we briefly describe how the Wn method can be applied to the problem of detecting clusters of putative transfers in genomic sequences: instead of computing the feature vector $\phi(.)$ for an individual gene, the computation is carried out across the extent of a sliding window that extends over multiple neighboring genes simultaneously.

The size of the window, i.e. the number of genes that are included in the computation of the feature vector $\phi(.)$ is a parameter of the algorithm. A score is obtained for each placement of the window, and the score of each gene is simply the average of the scores generated by all the windows in which the gene participates.

The Wn Method for LGT Detection: Automated Threshold Selection

Figure 6:
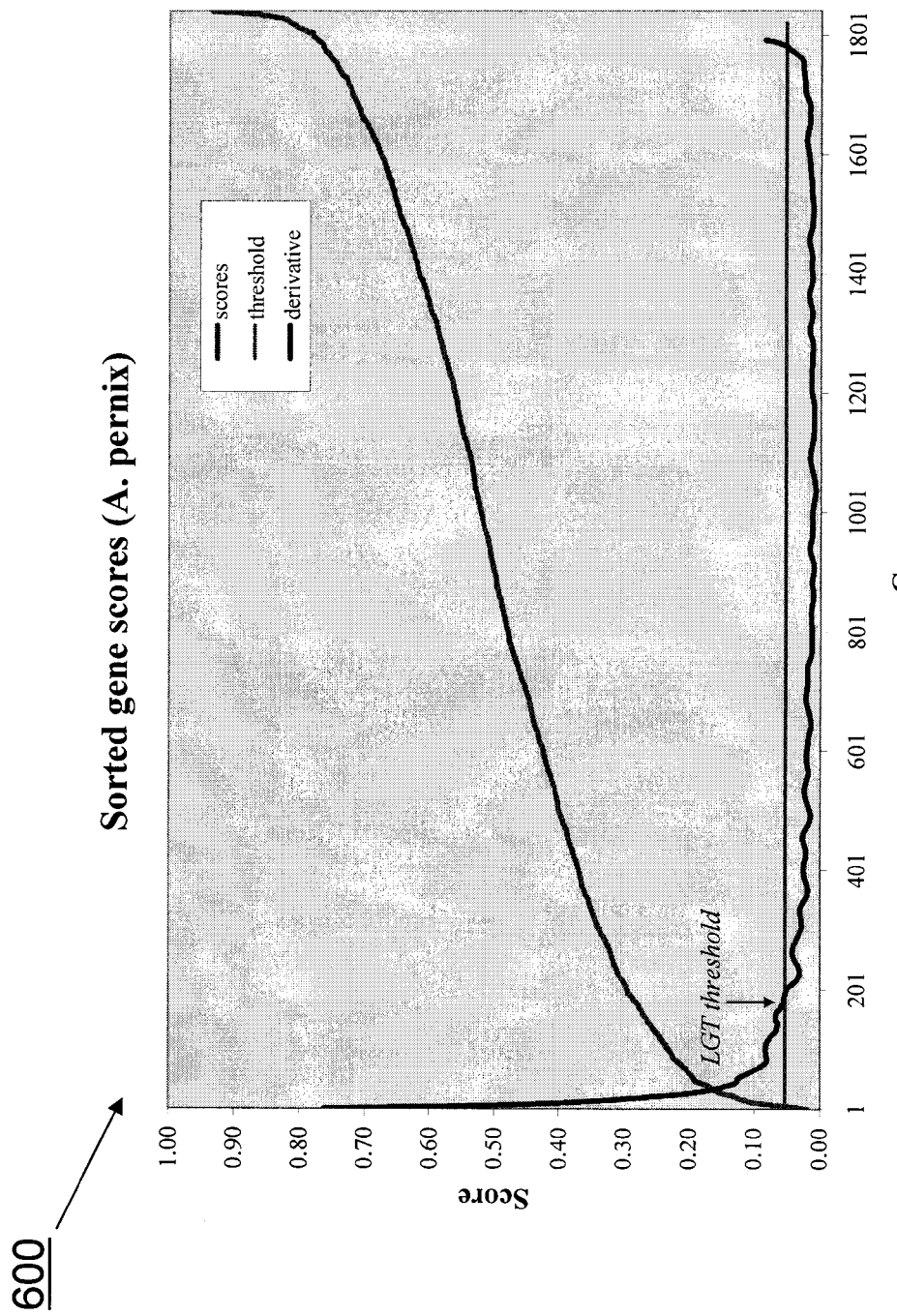
FIG. 6 is an exemplary graph 600 from the experimental data that illustrates the LGT threshold using the genomic sequence of Aeropyrum pemix as the input.
Figure 7:
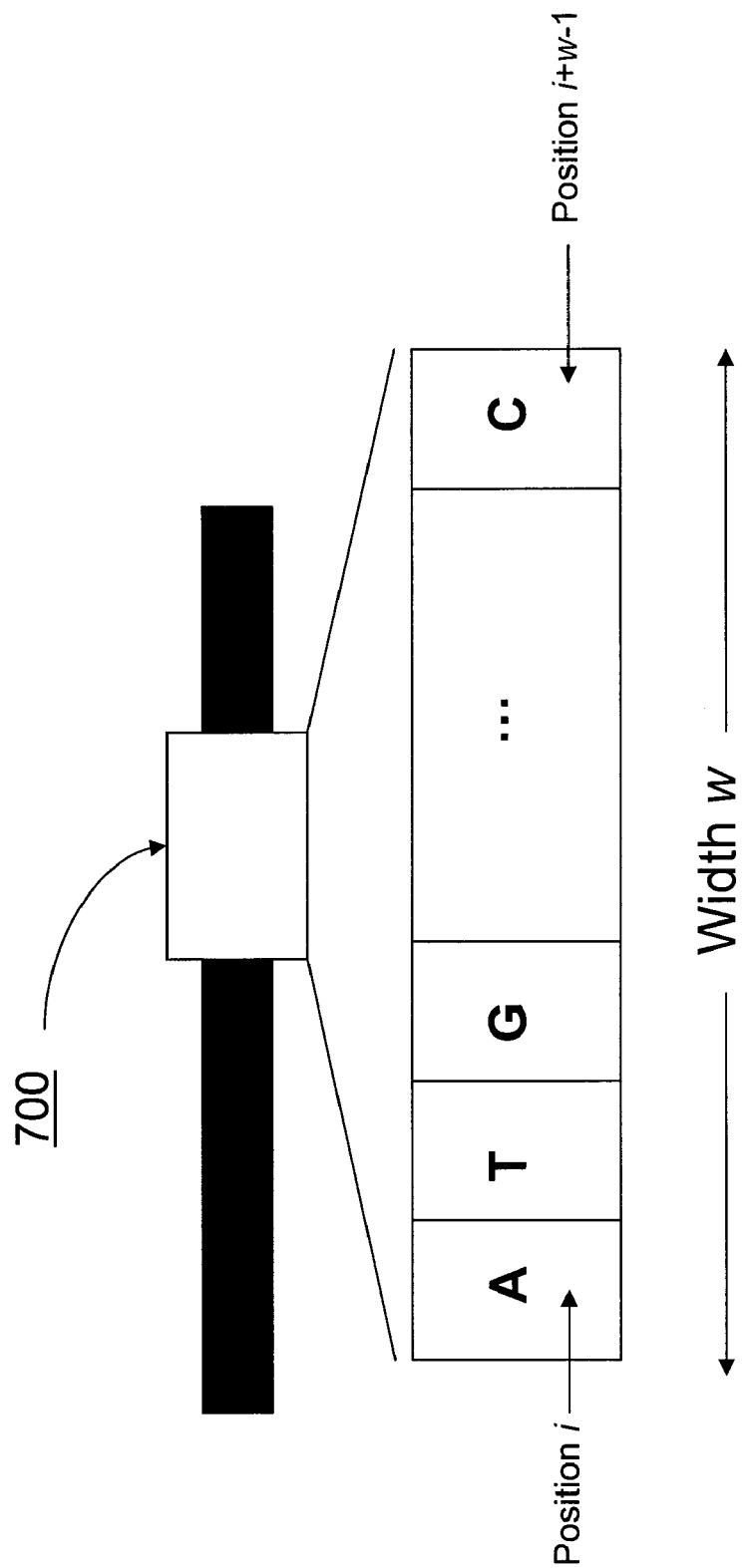
FIG. 7 exemplarily illustrates a template 700 used in the present invention having word width n.

Given the typicality scores for each sequence fragment g, there is also a need for the automatic determination of a threshold value: any sequence fragment g that falls below this threshold is then considered to be a horizontal transfer. We illustrate the process of automatically deciding the threshold using the typicality scores for each of the genes contained in the genome of A. pernix. The distribution of the scores f, sorted in increasing order, is shown in FIG. 6. In the same Figure, the derivative f' of the distribution is also shown, properly smoothed by taking the average over sliding windows. It is observed that the scores drop very fast for the first few genes, and then the derivative almost drops to zero. The following threshold T is defined based on the values of the derivatives f':

$$T = \min_i f'(i) + 2[\mathrm{avg}_i f'(i) - \min_i f'(i)]$$

The smallest value of i for which the derivative drops below threshold T represents the number of predicted putative horizontal gene transfers for the genome at hand.

Experiments and Results

Below, we demonstrate the potential of using compositional features to detect atypical sequence fragments through a very large number of experiments where we created artificial horizontal gene transfer events. The experimental procedure had as follows:

first, we created a pool of donor genes. Alternatively, one could have formed the pool of donors by forming a collection of variable size genomic fragments from a variety of genomes. The pool of donor genes that we used comprised the gene complement of the 27 phages shown in Table 1 and contained a total of 1,485 donor genes.

then, for each genome G under consideration, i.e. for each reference sequence G, a group of $D_G$ genes was randomly subselected, with replacement, from the donor pool and incorporated into the host genome under consideration. The number $D_G$ of the artificial transfer events was selected to be a fixed percentage of the number of genes contained in G, the host genome. Each genome in turn, from a collection of 123 fully-sequenced prokaryotic genomes (archaea and bacteria), served as a host genome for these experiments.

The purpose of this simulation was to recover as many as possible of the $D_G$ genes that we artificially incorporated in the genome G. In order to generate trustworthy estimates of the achieved performance, we repeated the above experiment a total of k=100 times for each one of the genomes G, and averaged the results. Finally, and in an effort to gauge the performance of our method for different amounts of horizontally transferred genes, we repeated the above experiments for different "mixture" percentages, i.e. for values of $D_G$ that ranged from 1% to 8% of the number of genes originally contained in the genome G.

Clearly, the $D_G$ genes that were incorporated in genome G during our simulation would be competing for the same positions with those horizontally transferred genes, if any, that are already present in G. Since all of the tested methods had to process the same input sets, the testing conditions were consistent across all used methods.

Each of the tested methods generated a typicality score for each gene, using the tested method's compositional features. The methods were then evaluated according to the percentage of genes from the phage donor pool that occupied the $D_G$-lowest typicality scores. We refer to this percentage as the "hit ratio."

Let m be a gene-scoring method, and $r_i^m(G)$ be the method's hit ratio as this is estimated from the i-th experiment, i=1, 2, 3 ..., k, with host genome G. We calculate the performance of method m on genome G to be the average across the k experiments:

$$r^m(G) = \frac{1}{k}\sum_{i=1}^{k} r_i^m(G)$$

With the help of $r_i^m(G)$, we calculate the overall performance of method m to be the average performance across the N genomes G used in our experiments:

$$r^m = \frac{1}{N}\sum_{G} r^m(G)$$

We evaluated the above performance values for several methods m. In Table 2, we show results for five methods: four of these methods were proposed in earlier work, whereas the fifth method is the Wn method of the present invention. As can be seen from this Table, Wn outperforms all four other methods.

The first method whose performance is listed in Table 2 is the *Codon Adaptation Index* (CAI); the latter is computed for each gene and becomes the gene's score. The lower this score is, the more atypical the gene is considered to be compared to the rest of the genome. The CAI index for gene g in genome G is given by the following formula:

$$CAI(g) = \exp\left(\sum_{i} f_i \ln W_i\right)$$

where $f_i$ is the relative frequency of codon i in the coding sequence, and $W_i$ the ratio of the frequency of codon i to the frequency of the major codon for the same amino-acid in the whole genome.

In the second method, the G+C content for each gene is computed and compared against the G+C content of the genome using the $\chi^2$ test; the $\chi^2$ value is negated in order to yield the gene typicality score.

The third method, labeled ¾ heretofore, is based on the composition of the dinucleotides comprising the nucleotides in the third codon position and the first position of the following codon. Again the $\chi^2$ test is used to compute the gene scores.

The remaining two methods, CODONS and W6 (e.g., the method of the present invention) use correlation as a similarity metric and templates of size 3 and 6 respectively as compositional features. In the case of CODONS, only tri-nucleotides that correspond to codons are taken into account. On the other hand, in the case of W6, all 6-nucleotide templates are counted.

In Table 3, the performance of all 5 methods is shown in absolute terms and for different percentages of artificially-transfered genes. In all cases, the W6 method, which is the method of the present invention, outperforms the rest. FIG. 1 summarizes pictorially the results contained in Table 3. Table 4 shows the performance of all 5 methods in relative terms.

Figure 2:
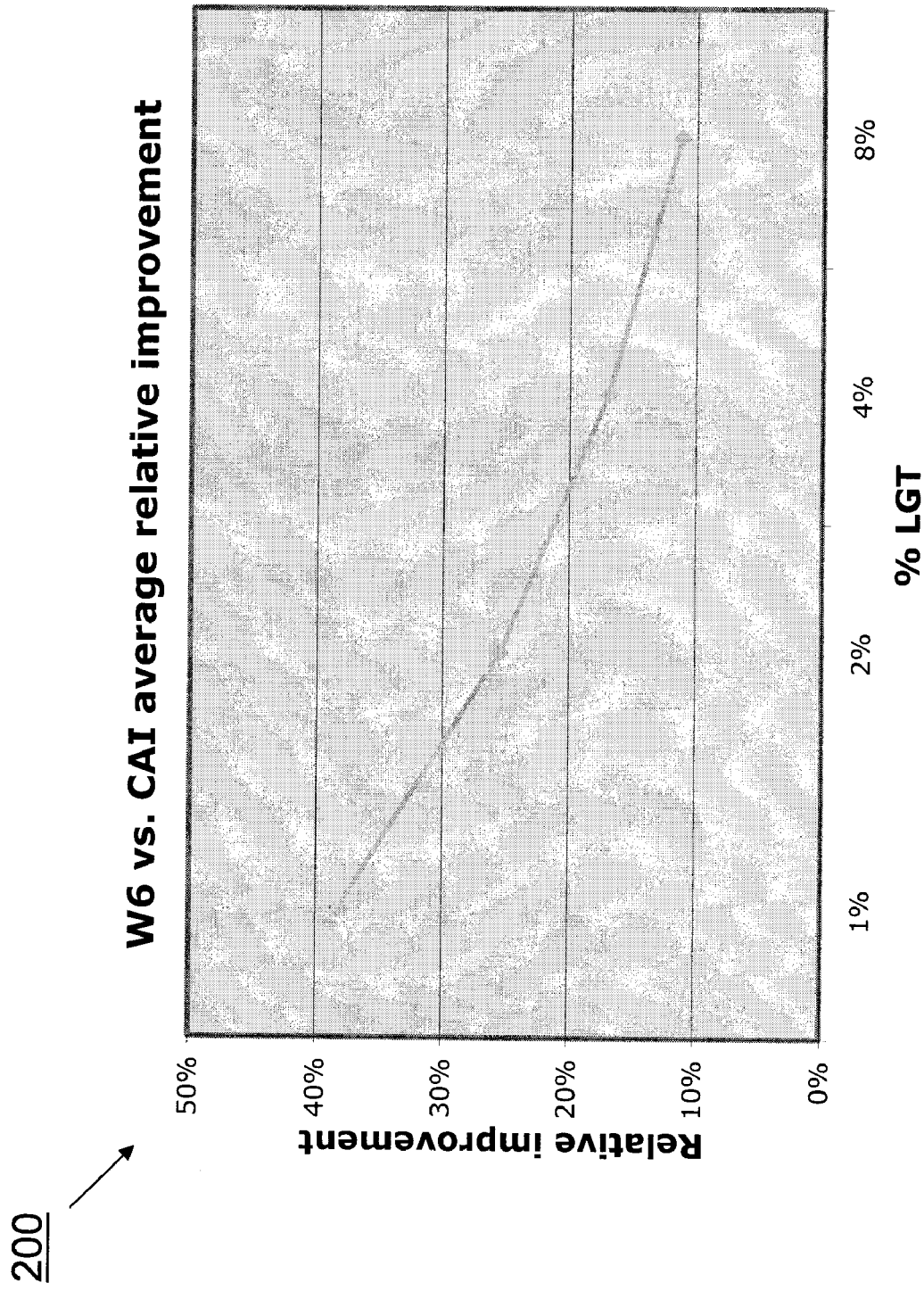
FIG. 2 shows the average relative improvement 200 of a specific instance of the present invention when compared with the second best performing conventional method (i.e., CAI), as a function of amount of artificially introduced LGTs.

Of the traditional methods, CAI has the best performance. But the method presented in the present invention outperforms CAI and leads to a relative improvement over CAI which ranges from 11% to 38%. Notably, the improvement of our method over the methods we have tested increases as the % of added genes decreases; in other words, Wn is particularly sensitive in those cases where the number of horizontally transferred genes is small compared to the number of genes comprising the genome G. FIG. 2 shows pictorially the average relative improvement of the Wn method of the present invention over CAI. For each organism, the relative increase in the hit ratio is calculated as $$R^m(G) = \frac{r^{W6}(G) - r^m(G)}{r^m(G)}$$

where m corresponds to the method that is used as a reference each time. The average relative improvement is obtained by taking the mean of the relative increase in the hit ratio across all organisms:

$$R^m = \frac{1}{N}\sum_{G} R^m(G)$$

This last figure is a measure of how many additional horizontal transfer events are detected when the Wn method of the present invention is compared with method m. For example, in the experiments with 2% added genes, the Wn method discovers an average of 25% more artificially transferred genes than CAI, and about 66% more than the G+C method.

Figure 3:
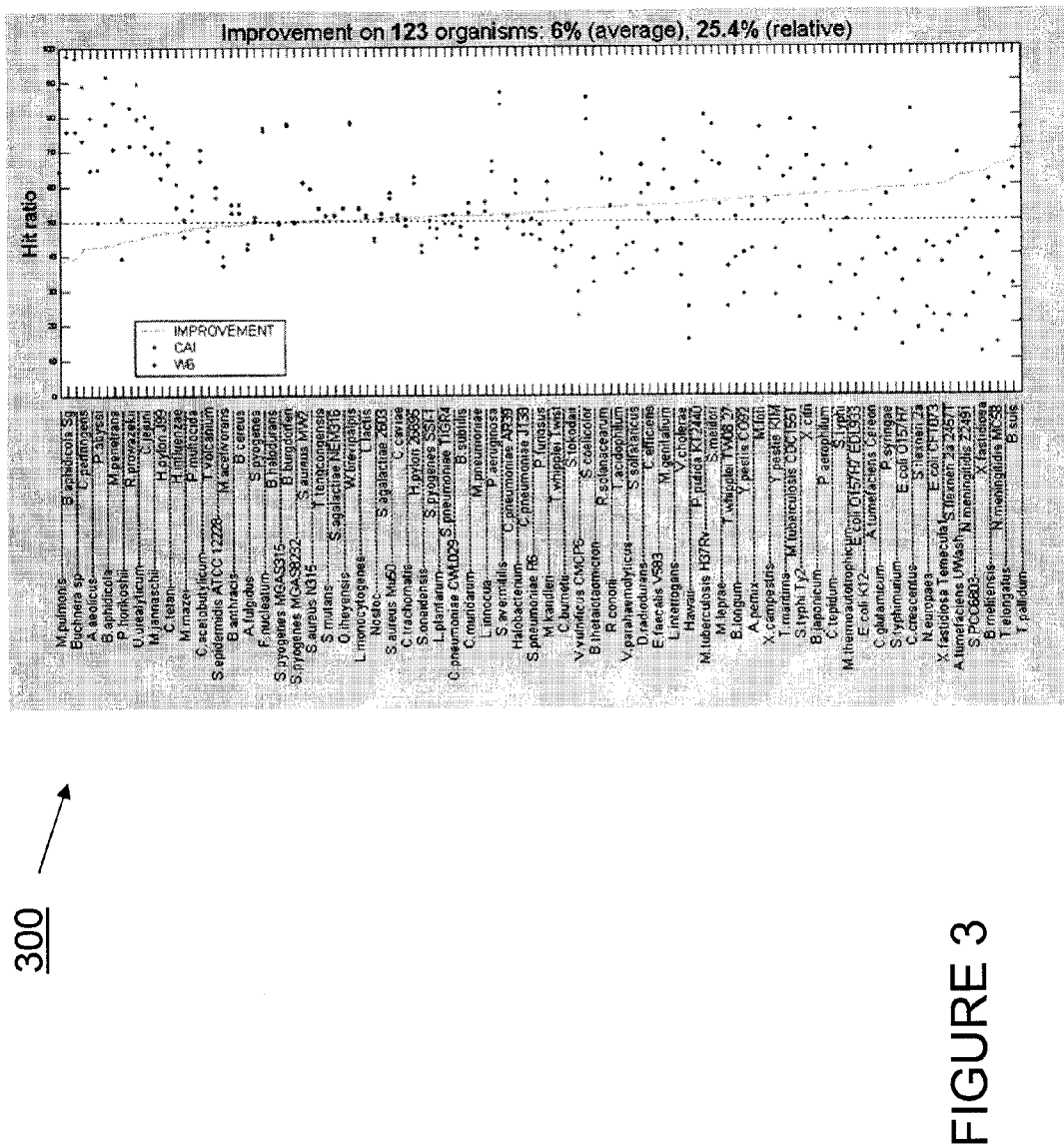
FIG. 3 shows the improvement 300 of a specific instance of the present invention relative to the second best performing conventional method (CAI) for each of 123 genomes that were used in the experiments.
Figure 4:
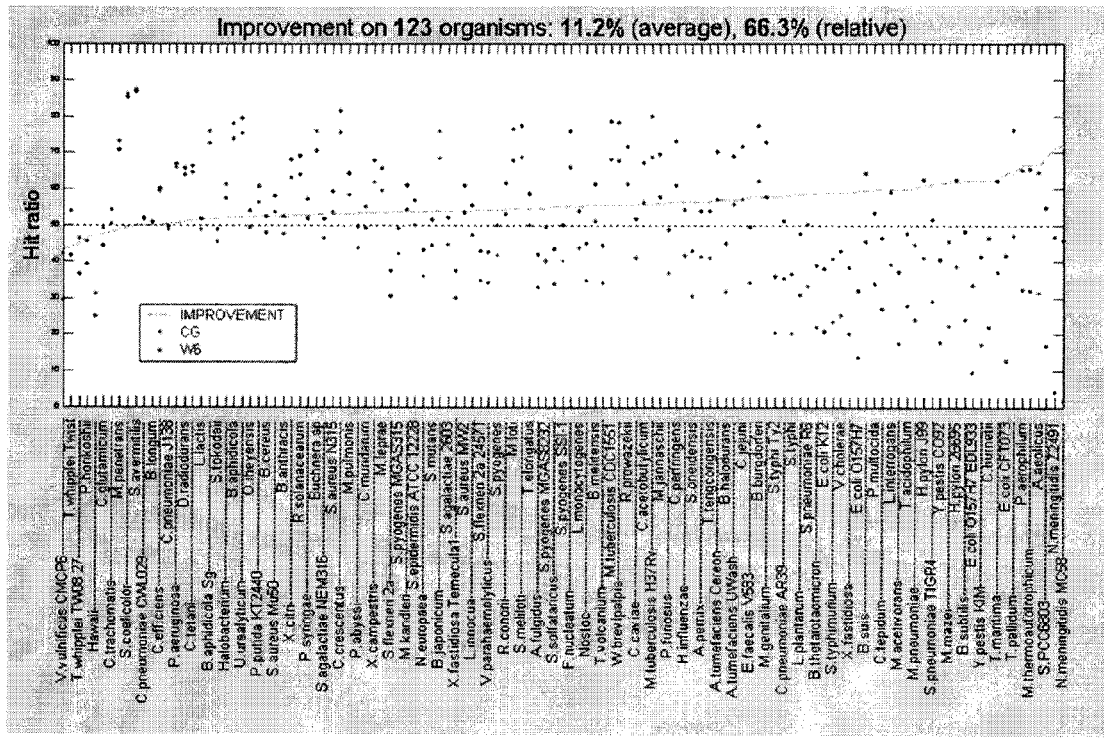
FIG. 4 shows the improvement 400 of a specific instance of the present invention relative to the next best performing conventional method (CG) for each of 123 genomes that were used in the experiments.

In FIG. 3, a detailed comparative analysis is shown of the performance of the inventive method and the CAI method for the experiments we carried out using a 2% mixture. For each organism, the performance of the Wn method is marked with a dot, and the performance of the CAI method with a "+". The curve shows the relative improvement achieved by our method across organisms. For visualization purposes, the 123 genomes are listed in order of increasing relative improvement achieved by Wn. On the left side of the graph, where the line assumes negative values, the CAI method outperforms the Wn method, whereas on the right side the Wn method greatly outperforms the CAI method. In fact, for the majority of the organisms (91 versus 32) the Wn method of the present invention provides significantly improved performance over the CAI method. FIG. 4 shows the same kind of comparative analysis but this time the Wn method is compared with G+C method.

In additional experiments, we also studied the effect of template size (i.e. the n in Wn) on the overall performance of the Wn method. Using the above experimental protocol with 100 experiments per organism, we discovered that for template sizes greater than 2, the optimal performance was achieved by a) ignoring the periodicity of the genetic code and by b) choosing correlation as the similarity metric for computing the final scores.

Figure 5:
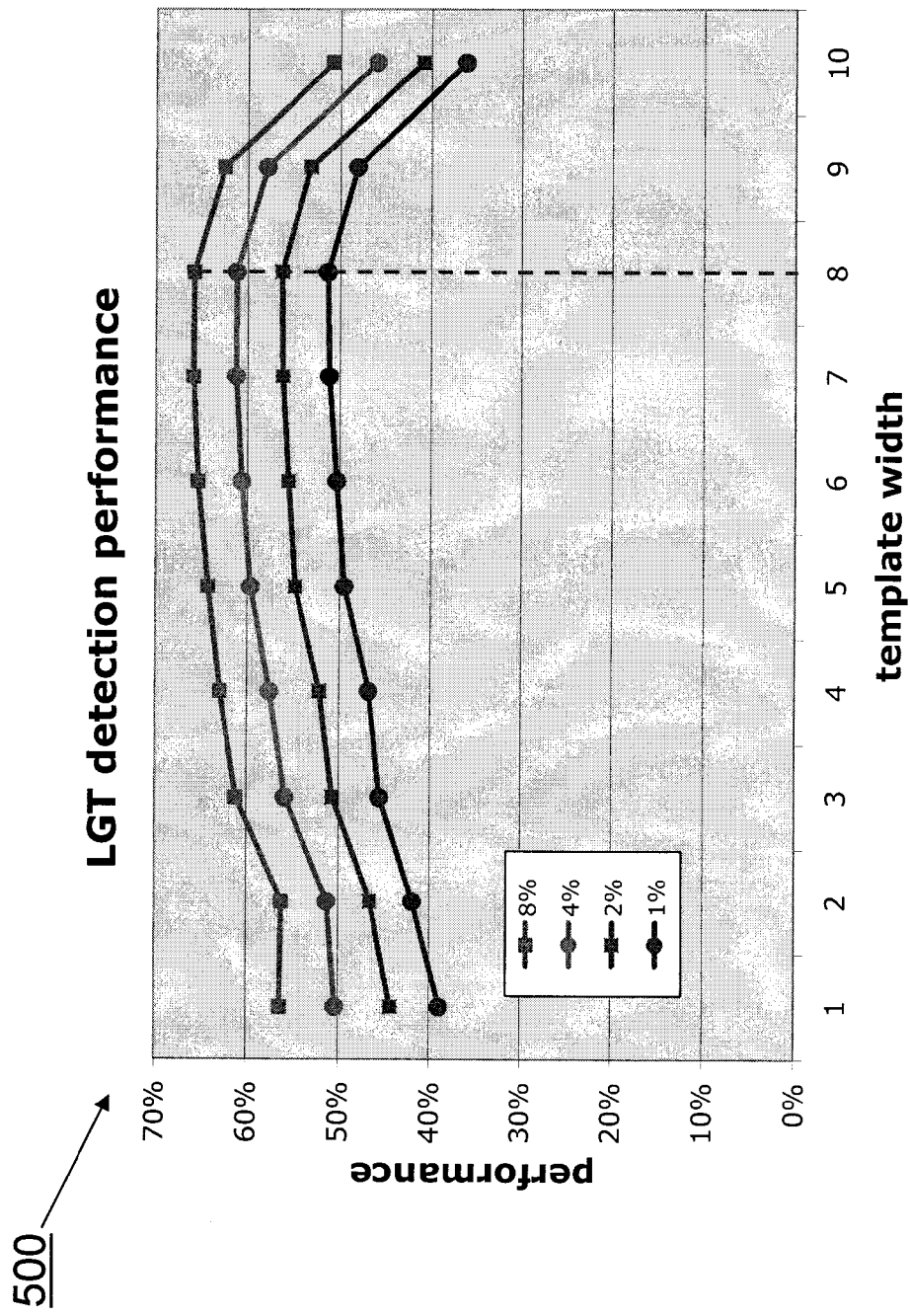
FIG. 5 shows the result 500 of LGT detection by the present invention as a function of the length n of the template used and for various amounts of artificially introduced LGTs.

FIG. 5 shows how the optimal feature/metric combination affects the gene detection performance as a function of the size n of the template. Initially, as the template size increases performance improves reaching a maximum value at sizes 6 through 8. However, any further increases in the size of the template lead to a degradation of performance. The choice of the template size to use depends in turn on the size of the sequence fragment g. In order to achieve high specificity, the largest possible template size should be opted for, provided that the sequence fragment g is sizeable enough to yield a substantial number of templates of the chosen size. Large template sizes should also be used with the sliding window variant and large windows. On the other hand, a smaller size template should be used when individual gene transfers are sought.

Following is a discussion of the exemplary inventive method as optionally implemented in software and/or hardware. First, as explained above and exemplarily shown in FIG. 7, the template of the present invention is a word of characters having width n, where n>=3, and where the characters are allowed to include a "." or "don't care" symbol. Moreover, templates can be formed in position-specific manner.

Figure 8:
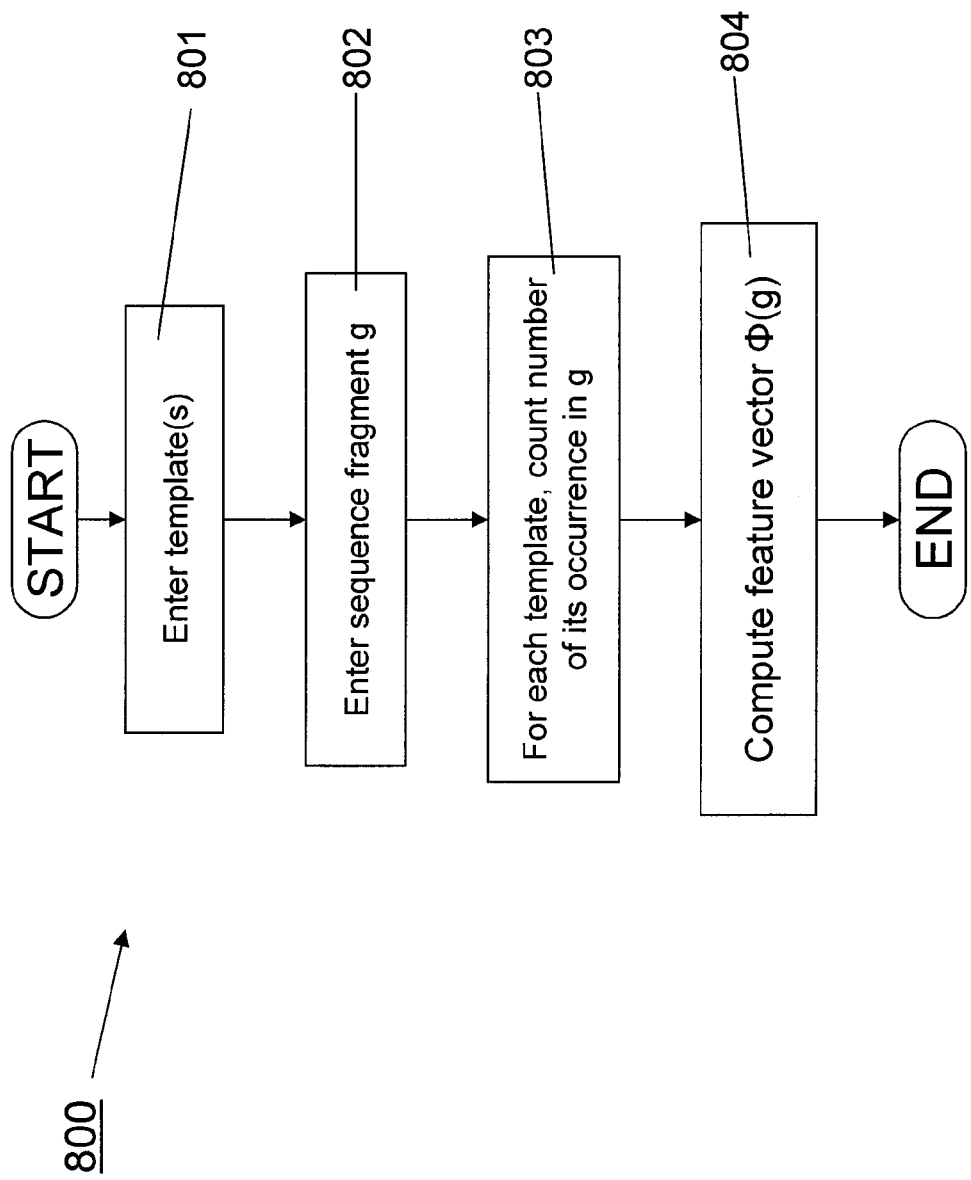
FIG. 8 illustrates an exemplary flowchart 800 of a software program to derive the compositional feature vector used in the present invention.

FIG. 8 illustrates an exemplary flowchart of a method 800 for determining the template counts and for calculating the compositional feature vector φ(g) of a sequence fragment g. In step 801, data for at least one template Wn is entered. As explained above, more than one template can be entered so that a set of templates $\pi=\{\pi_1, \pi_2, \ldots, \pi_q\}$ can be counted in parallel.

In step 802, data from the sequence fragment g is retrieved from memory and, in step 803 the number of occurrences in g of each template is determined. If the template occurrence data is to be converted into the compositional feature vector format $\phi(s)=(\alpha_1, \alpha_2, \ldots, \alpha_q)$, discussed above, where $\alpha_i$ is the frequency of template $\pi_i$ in g, then this data conversion is performed in step 804.

Figure 9:
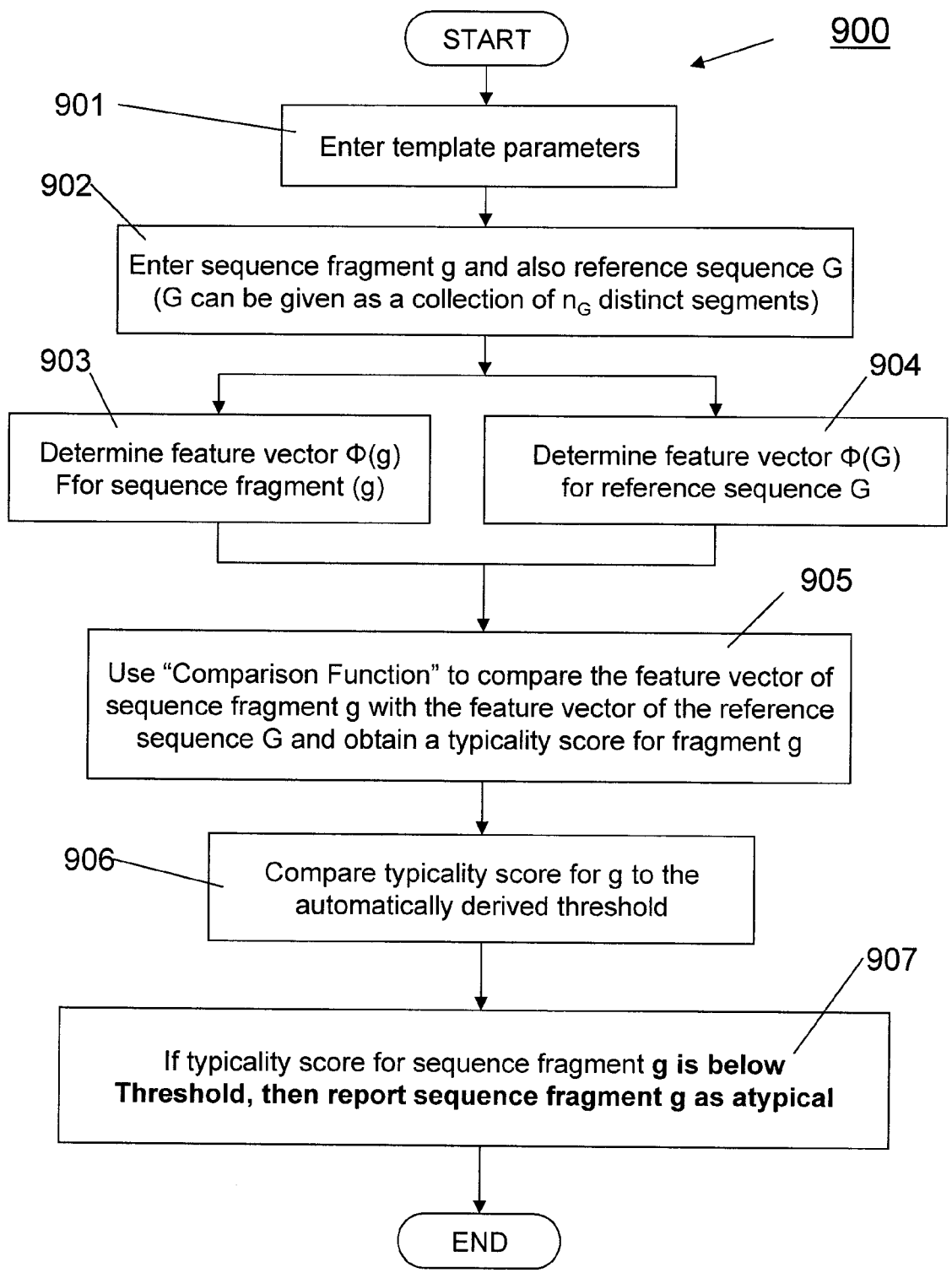
FIG. 9 illustrates an exemplary flowchart 900 of a software program to derive the typicality scores (and LGT likelihood) for each sequence fragment of interest.

FIG. 9 illustrates an exemplary flowchart 900 that can be used to compute the calculations for the atypicality score a sequence fragment g. In step 901 template data are entered. In step 902, a sequence fragment g and a reference sequence G are entered. In steps 903 and 904 the compositional feature vector φ(g) for sequence fragment g and the compositional feature vector φ(G) for reference sequence G are calculated, as discussed above for the steps exemplarily shown in FIG. 8. If the reference sequence G is a collection of $n_G$ distinct segments, then the compositional feature vector φ(G) can be calculated as the average of the compositional feature vectors of its segments.

In step 905, a "comparison" function is applied to determine for the sequence fragment g its atypicality with respect to the reference sequence G. As mentioned above, a number of similarity measures can be used and the present invention is not intended to be limited in the specific measure to be used. Thus, for example, this step 905 can be executed using any of a number of schemes including the classic Pearson correlation, standard $\chi^2$ values, Mahalanobis distance, the Kullback-Liebler distance, etc.

In step 906, the typicality score for g is compared with the automatically derived threshold value, such as discussed above. Finally, in step 907, if the typicality score for g is below threshold, then the fragment g will be reported as atypical.

Figure 10:
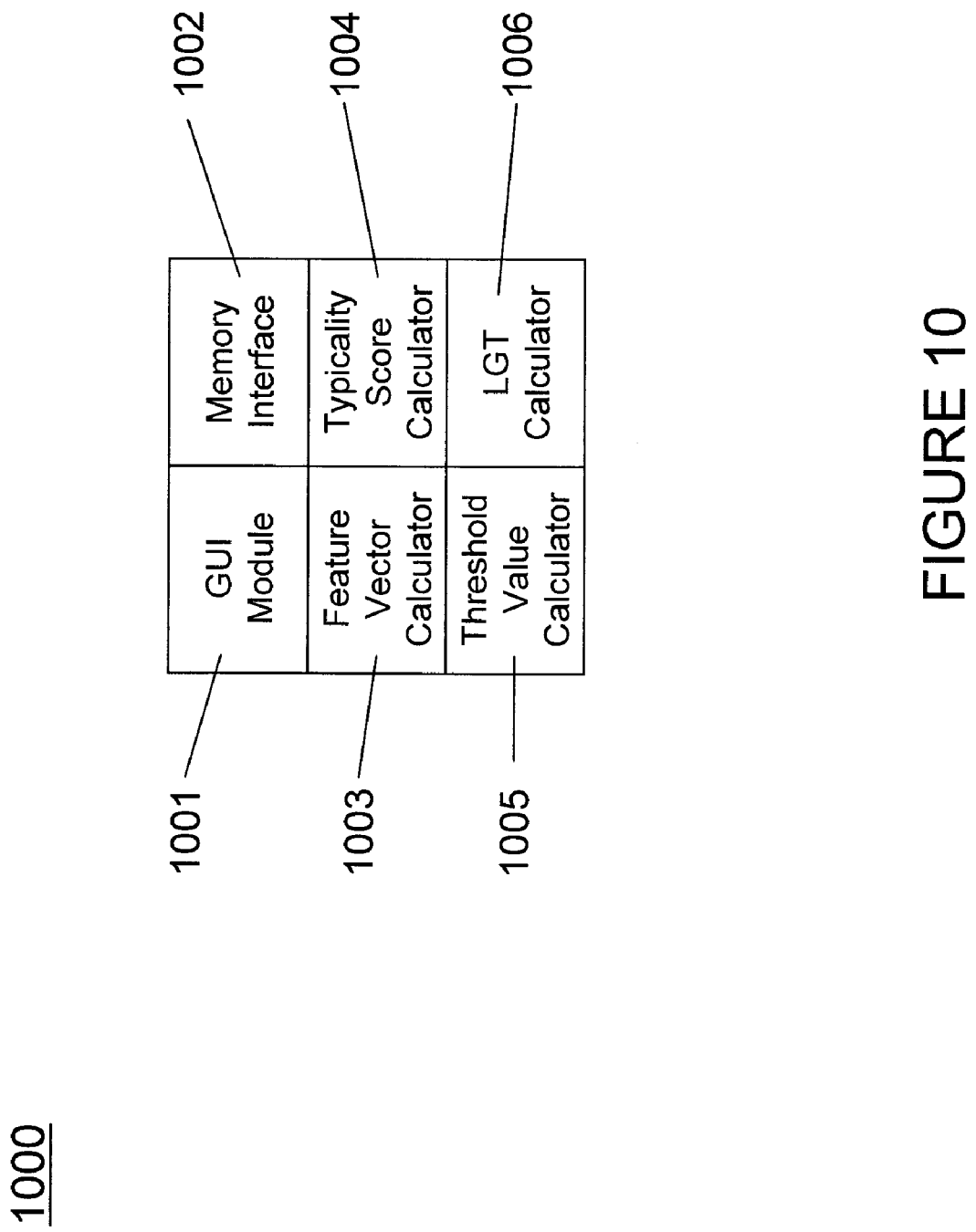
FIG. 10 illustrates an exemplary block diagram 1000 of a software module for executing the present invention.

FIG. 10 illustrates an exemplary block diagram 1000 of a system of software modules for a computer implementation of the present invention. This system would include a graphical user interface 1001 to allow a user to enter template data and provide other system controls. Memory interface module 1002 allows data from a database to be entered for evaluation and results to be stored throughout the execution. Feature vector calculator module 1003 determines the process described in FIG. 8, and typicality score module 1004, threshold value module 1005, and LGT calculator module 1006 executes the equations discussed above for their respective values.

Figure 11:
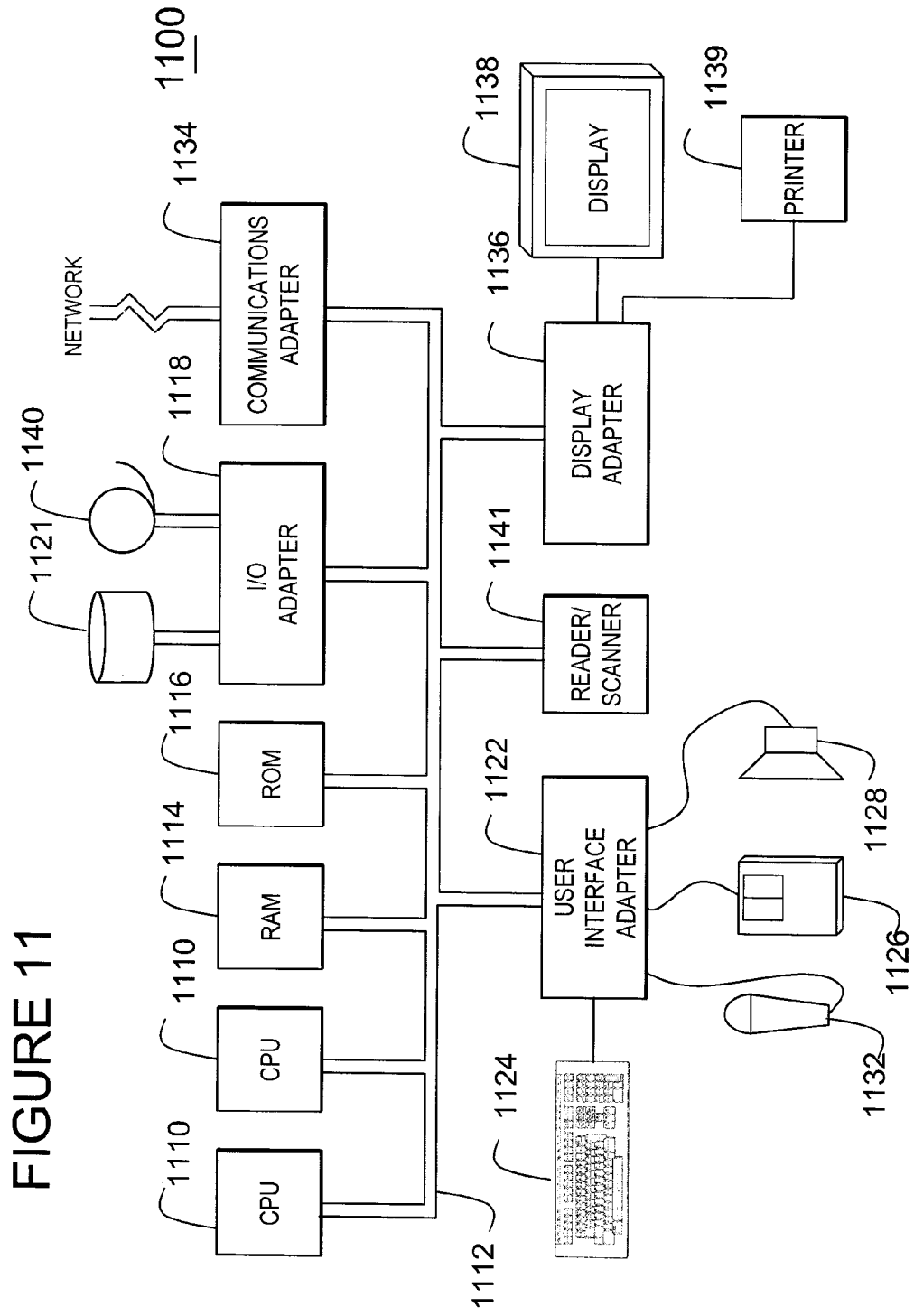
FIG. 11 illustrates an exemplary hardware/information handling system 1100 for incorporating the present invention therein.
Figure 12:
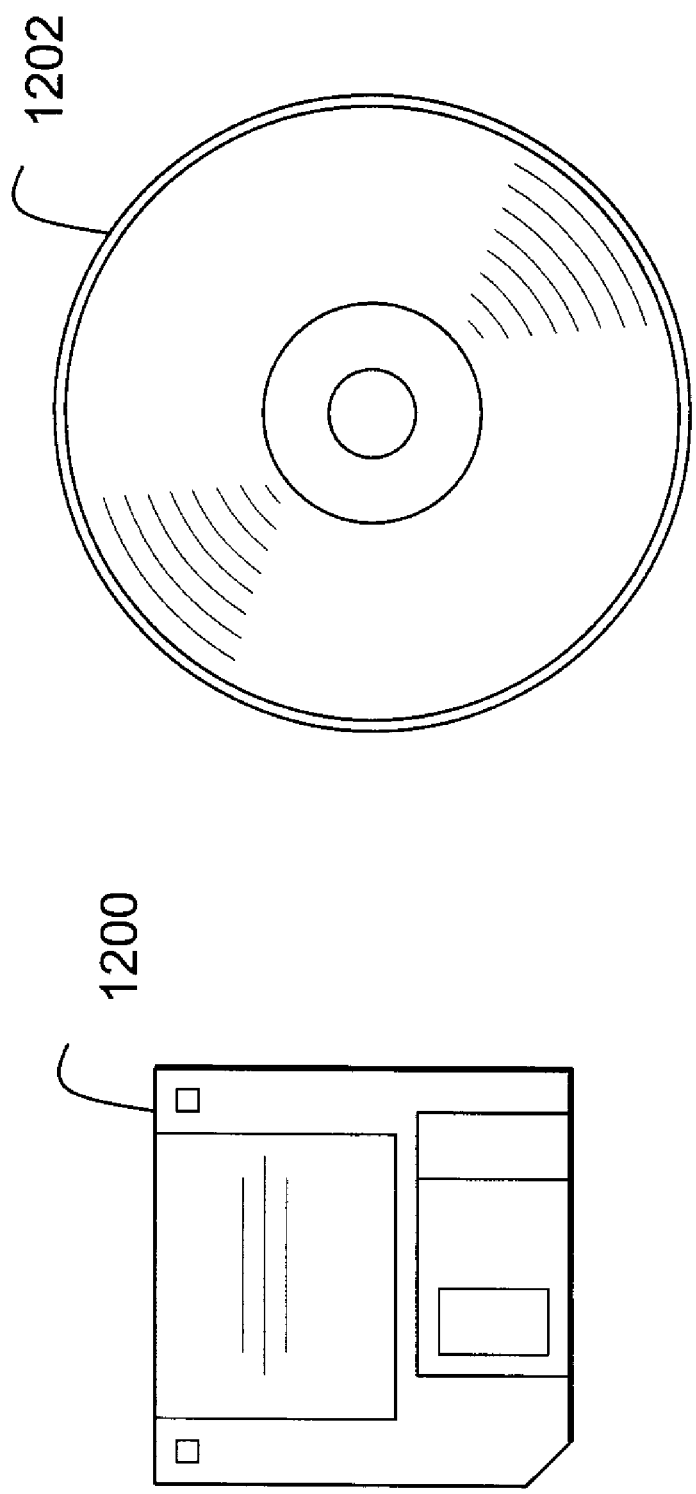
FIG. 12 illustrates a signal bearing medium 1200 (e.g., storage medium) for storing steps of a program of a method according to the present invention.

FIG. 11 illustrates a typical hardware configuration of an information handling/computer system in accordance with the invention and which preferably has at least one processor or central processing unit (CPU) 1111.

The CPUs 1111 are interconnected via a system bus 1112 to a random access memory (RAM) 1114, read-only memory (ROM) 1116, input/output (I/O) adapter 1118 (for connecting peripheral devices such as disk units 1121 and tape drives 1140 to the bus 1112), user interface adapter 1122 (for connecting a keyboard 1124, mouse 1126, speaker 1128, microphone 1132, and/or other user interface device to the bus 1112), a communication adapter 1134 for connecting an information handling system to a data processing network, the Internet, an Intranet, a personal area network (PAN), etc., and a display adapter 1136 for connecting the bus 1112 to a display device 1138 and/or printer 1139 (e.g., a digital printer or the like).

In addition to the hardware/software environment described above, a different aspect of the invention includes a computer-implemented method for performing the above method. As an example, this method may be implemented in the particular environment discussed above.

Such a method may be implemented, for example, by operating a computer, as embodied by a digital data processing apparatus, to execute a sequence of machine-readable instructions. These instructions may reside in various types of signal-bearing media.

Thus, this aspect of the present invention is directed to a programmed product, comprising signal-bearing media tangibly embodying a program of machine-readable instructions executable by a digital data processor incorporating the CPU 1111 and hardware above, to perform the method of the invention.

This signal-bearing media may include, for example, a RAM contained within the CPU 1111, as represented by the fast-access storage for example. Alternatively, the instructions may be contained in another signal-bearing media, such as a magnetic data storage diskette 1200 (FIG. 12), directly or indirectly accessible by the CPU 1111.

Whether contained in the diskette 1200, the computer/CPU 1111, or elsewhere, the instructions may be stored on a variety of machine-readable data storage media, such as DASD storage (e.g., a conventional "hard drive" or a RAID array), magnetic tape, electronic read-only memory (e.g., ROM, EPROM, or EEPROM), an optical storage device (e.g. CD-ROM, WORM, DVD, digital optical tape, etc.), paper "punch" cards, or other suitable signal-bearing media including transmission media such as digital and analog and communication links and wireless. In an illustrative embodiment of the invention, the machine-readable instructions may comprise software object code.

Thus, the present invention provides a new method Wn for atypicality detection that is based on generalized compositional features. Given a reference sequence G and a sequence fragment g the method assigns the latter a score that reflects its similarity to the reference sequence G. For the specific instance of the invention where the involved sequences were genetic sequences, it was found that CAI and W6 scores yield the best performance, with W6 outperforming CAI. W6 is the exemplary method of the present invention. The performance of various methods including CAI and W6 was measured through a series of experiments where a random set of genes from phages was added to each of a fully-sequenced prokaryotic genome in turn, thus creating an artificial organism, with the objective of recovering in the lowest scoring positions as many of the added genes as possible without any a priori knowledge.

While the invention has been described in terms of a single preferred embodiment, those skilled in the art will recognize that the invention can be practiced with modification within the spirit and scope of the appended claims.

Further, it is noted that, Applicants' intent is to encompass equivalents of all claim elements, even if amended later during prosecution.

Having thus described our invention, what we claim as new and desire to secure by Letters Patent is as follow:

1. An apparatus for determining that a sequence fragment is atypical with respect to a reference sequence, comprising:
    a compositional feature vector calculator to compute a number of occurrences of a given template having at least two template characters in a genetic sequence fragment under evaluation, said number of occurrences used to determine whether said genetic sequence fragment is atypical;
    a memory interface to retrieve said genetic sequence fragment under evaluation from a memory and to record said number of occurrences of said template in said genetic sequence fragment under evaluation;
    a processor to compare elements of said template sequentially with elements of said genetic sequence fragment under evaluation and to determine matches at each sequential position along said genetic sequence fragment under evaluation; and
    a display to selectively display information related to said number of occurrences,
    wherein an atypicality is determined based upon a similarity metric between said template and said genetic sequence fragment under evaluation.

2. The apparatus of claim 1, wherein said template includes a number of characters that is less than nine.

3. The apparatus of claim 2, wherein said number lies in a range of six to eight.

4. The apparatus of claim 1, wherein said template optionally includes at least one "don't care" character.

5. The apparatus of claim 1, further comprising:
    a graphical user interface to allow a user to enter data for said template and to selectively view said information related to said number of occurrences;
    a typicality score calculator module to calculate a typicality score for a sequence fragment on a reference sequence based on said number of occurrences; and
    a threshold value calculator module to calculate an atypicality threshold for the sequence fragment under evaluation.

6. The apparatus of claim 5, further comprising:
    a lateral gene transfer (LGT) calculator to determine whether said typicality score for said sequence fragment is below said threshold.

7. A machine-readable storage medium tangibly embodying a program of machine-readable instructions executable by a digital processing apparatus to perform a method of determining that a sequence fragment is atypical with respect to a reference sequence in an organism, said program comprising:
    a compositional feature vector calculator to compute a number of occurrences of a given template having at least two template characters in a genetic fragment under evaluation;
    a memory interface module to retrieve said genetic fragment under evaluation from a memory and to record said number of occurrences of said template in said genetic fragment under evaluation;
    a typicality score calculator module to calculate a typicality score based on said number of occurrences; and
    a graphical user interface module to selectively permit a user to enter data for said template and to selectively display information related to said number of occurrences,
    wherein an atypicality is determined based upon a similarity metric between said template and said genetic sequence fragment under evaluation.

8. The machine-readable storage medium of claim 7, wherein said template has a number of characters that is less than nine.

9. The machine-readable storage medium of claim 7, wherein said number lies in a range of six to eight.

10. The machine-readable storage medium of claim 7, wherein said template optionally includes at least one "don't care" character.

11. The machine-readable storage medium of claim 7, further comprising:
    a threshold value calculator module to calculate an atypicality threshold for said sequence fragment under evaluation.

12. The machine-readable storage medium of claim 11, further comprising:
    a lateral gene transfer (LGT) calculator module to determine whether said typicality score for said sequence fragment is below said threshold.

13. A system of determining that a sequence fragment g is atypical with respect to a reference sequence G, said system comprising:
    means for constructing at least one template, each said template containing a sequence of characters;
    means for counting a number of occurrences in said sequence g for each of said at least one template;
    means for counting a number of occurrences in said reference sequence G for each of said at least one template and determining whether said occurrence falls below a threshold that indicates atypicality; and
    means to selectively view information related to said number of occurrences,
    wherein a number of said characters contained in each of said at least one template exceeds two, and
    wherein an atypicality is determined based upon a similarity metric between said template and said genetic sequence fragment under evaluation.

14. The apparatus of claim 1, wherein said number of occurrences of said template in said genetic sequence fragment under evaluation comprises a measure of whether said genetic sequence fragment under evaluation is native to an organism's genome or represents an atypicality acquired through a gene transfer from another organism.

15. The apparatus of claim 5, wherein said typicality score comprises a similarity metric.

16. The apparatus of claim 15, wherein said similarity metric comprises one of:
    a correlation calculation;
    a $\chi^2$ test calculation;
    a Mahalanobis distance; and
    a relative entropy calculation.

* * * * *

UNITED STATES PATENT AND TRADEMARK OFFICE
CERTIFICATE OF CORRECTION

| | |
|---|---|
| PATENT NO. | : 7,613,662 B2 |
| APPLICATION NO. | : 10/855367 |
| DATED | : November 3, 2009 |
| INVENTOR(S) | : Tsirigos et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 512 days.

Signed and Sealed this

Nineteenth Day of October, 2010

David J. Kappos
*Director of the United States Patent and Trademark Office*